US012350093B2

(12) United States Patent
Isla Garcia

(10) Patent No.: US 12,350,093 B2
(45) Date of Patent: Jul. 8, 2025

(54) APPARATUS AND METHOD FOR TRACKING BLOOD VESSEL CROSS-SECTION

(71) Applicant: EDWARDS LIFESCIENCES CORPORATION, Irvine, CA (US)

(72) Inventor: Julio Agustin Isla Garcia, Irvine, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 18 days.

(21) Appl. No.: 18/181,235

(22) Filed: Mar. 9, 2023

(65) Prior Publication Data

US 2023/0277157 A1    Sep. 7, 2023

Related U.S. Application Data

(63) Continuation of application No. PCT/US2021/049355, filed on Sep. 8, 2021.

(60) Provisional application No. 63/076,155, filed on Sep. 9, 2020.

(51) Int. Cl.
*A61B 8/08* (2006.01)
*A61B 8/00* (2006.01)

(52) U.S. Cl.
CPC .......... *A61B 8/0891* (2013.01); *A61B 8/4477* (2013.01)

(58) Field of Classification Search
CPC .................. A61B 8/0891; A61B 8/4477
See application file for complete search history.

(56) References Cited

U.S. PATENT DOCUMENTS

| | | | |
|---|---|---|---|
| 6,677,985 B1* | 1/2004 | Kubota | G01S 7/52073 600/441 |
| 2004/0193041 A1* | 9/2004 | Ostrovsky | A61B 5/062 600/467 |
| 2014/0066765 A1* | 3/2014 | Fan | A61B 8/0891 600/407 |
| 2014/0236011 A1* | 8/2014 | Fan | A61B 8/4477 600/407 |
| 2014/0270436 A1* | 9/2014 | Dascal | A61B 5/0073 382/130 |
| 2015/0245820 A1* | 9/2015 | Tamada | G16H 50/30 600/449 |
| 2015/0250448 A1* | 9/2015 | Tamada | A61B 8/5223 600/449 |
| 2015/0289836 A1* | 10/2015 | Mizukami | G16H 50/30 600/438 |

(Continued)

*Primary Examiner* — Dixomara Vargas
(74) *Attorney, Agent, or Firm* — Getz Balich LLC

(57) ABSTRACT

A system and method for tracking a cross-section geometry of a blood vessel is provided. The system includes at least one sensor a plurality of ultrasonic transducers and a controller. The ultrasonic transducers are configured to non-invasively sense a blood vessel and provide signals representative of the blood vessel. The controller is in communication with the at least one sensor and a non-transitory memory storing instructions. The instructions when executed cause the controller to: a) control the plurality of ultrasonic transducers to periodically sense the blood vessel and produce signals representative of a plurality of features of the blood vessel; and b) track the plurality of features of the blood vessel, using the signals representative of the plurality of features to determine a cross-section geometry of the blood vessel as a function of time.

13 Claims, 8 Drawing Sheets

(56) References Cited

U.S. PATENT DOCUMENTS

| | | | |
|---|---|---|---|
| 2019/0046152 A1* | 2/2019 | Siedenburg | A61B 8/0891 |
| 2019/0090852 A1* | 3/2019 | Kroon | A61B 8/4245 |
| 2022/0175340 A1* | 6/2022 | Xu | A61B 8/4444 |
| 2023/0255600 A1* | 8/2023 | Huang | A61B 8/485 |
| | | | 600/438 |

* cited by examiner

=

APPARATUS AND METHOD FOR TRACKING BLOOD VESSEL CROSS-SECTION

RELATED APPLICATION

This application claims the benefit of PCT/US2021/049355 filed on Sep. 8, 2021, which claims priority based on U.S. Provisional Patent Application Ser. No. 63/076,155, filed Sep. 9, 2020, and entitled APPARATUS AND METHOD FOR TRACKING BLOOD VESSEL CROSS-SECTION, the complete disclosures of which are hereby incorporated herein in their entireties.

BACKGROUND OF THE INVENTION

1. Technical Field

The present disclosure relates to systems and methods for tracking blood vessel cross-sections in general, and systems and methods for non-invasively tracking blood vessel cross-sections in particular.

2. Background Information

The ability to determine the cross-section geometry of a blood vessel is useful for a variety of different purposes. It is known to use ultrasonic sensing to determine the location of a blood vessel; e.g., see U.S. Patent Publication No. 2019/0099153. Currently known methods, however, produce vessel cross-sectional information generically, or fail to perform satisfactorily with some specific vessel features, or are slow and therefore not suitable for real-time operation, or lack the very high accuracy required for the tracking of very small changes, or combinations thereof. Real-time accurate tracking performance is central to providing uninterrupted, continuous physiological measurements. What is needed is a system and/or method that can accurately track very small changes in vessel geometry in real-time, and thereby provide the information needed to provide uninterrupted, continuous physiological measurements.

SUMMARY

According to an aspect of the present disclosure, a system for tracking a cross-section geometry of a blood vessel is provided. The system includes at least one sensor a plurality of ultrasonic transducers and a controller. The ultrasonic transducers are configured to non-invasively sense a blood vessel and provide signals representative of the blood vessel. The controller is in communication with the at least one sensor and a non-transitory memory storing instructions. The instructions when executed cause the controller to: a) control the plurality of ultrasonic transducers to periodically sense the blood vessel and produce signals representative of a plurality of features of the blood vessel; and b) track the plurality of features of the blood vessel, using the signals representative of the plurality of features to determine a cross-section geometry of the blood vessel as a function of time.

In aspects or embodiments described above and herein, the signals produced by the plurality of ultrasonic transducers signals may represent an ultrasonic image of the blood vessel.

In any of the aspects or embodiments described above and herein, the instructions when executed may cause the controller to assign a plurality of tracking windows to at least one of the plurality of features for each of a plurality of periodic frames, and the step of tracking the plurality of features of the blood vessel as a function of time includes tracking a respective one of the plurality of features within a first tracking window from a first frame to a corresponding second tracking window from a second frame, the second frame subsequent to the first frame, and the instructions when executed may cause the controller to determine a first blood vessel diameter within the first frame and a second first blood vessel diameter within the second first frame.

In any of the aspects or embodiments described above and herein, the instructions when executed may cause the controller to assign a plurality of first tracking windows to a first of the plurality of features, and a plurality of second tracking windows to a second of the plurality of features, and may cause the controller to track the first tracking windows and the second tracking windows in parallel.

In any of the aspects or embodiments described above and herein, the instructions when executed may cause the controller to assign a first plurality of windows to a first feature of the plurality of features within a first frame, and a second plurality of windows to the first feature within a second frame, the second frame subsequent to the first frame, and perform a two dimensional cross-correlation between the signals representative of the first feature within the first frame and the signals representative of the first feature within the second frame using at least one convex constraint.

In any of the aspects or embodiments described above and herein, the instructions when executed may cause the controller to assign a third plurality of windows to a second feature of the plurality of features within the first frame, and a fourth plurality of windows to the second feature within the second frame, and perform a two dimensional cross-correlation between the signals representative of the second feature within the first frame and the signals representative of the second feature within the second frame using at least one substantially convex constraint, and the first and second plurality of windows may be tracked in parallel with the third and fourth plurality of windows.

In any of the aspects or embodiments described above and herein, the two dimensional cross-correlation between the signals representative of the first feature within the first frame and the signals representative of the first feature within the second frame may be performed using a plurality of substantially convex constraints, each assigned a relative weight, and the two dimensional cross-correlation between the signals representative of the second feature within the first frame and the signals representative of the second feature within the second frame may be performed using a plurality of substantially convex constraints, each assigned a relative weight.

In any of the aspects or embodiments described above and herein, the plurality of ultrasonic transducers may include "N" number of ultrasonic transducers, where "N" is an integer, and each ultrasonic transducer is actuated to produce incident ultrasonic signals on a time delay basis from a preceding ultrasonic transducer, the time delay corresponds to an amount of time it takes the incident ultrasonic signal to travel from the sensor to the blood vessel and a reflected ultrasonic signal to travel back to the sensor.

In any of the aspects or embodiments described above and herein, the time delayed reflected signals may be added to produce a collective signal and a maximum portion of the collective signal corresponding to an anterior wall of the blood vessel and a maximum portion of the collective signal corresponding to a posterior wall may be multiplied.

In any of the aspects or embodiments described above and herein, for each of a plurality of possible positions of the blood vessel cross-section, the time delayed reflected signals may be added to produce a collective signal and a maximum portion of the collective signal corresponding to an anterior wall of the blood vessel and a maximum portion of the collective signal corresponding to a posterior wall may be multiplied to produce a maximum value.

In any of the aspects or embodiments described above and herein, the instructions when executed may cause the controller to compare the maximum value determined for each of the plurality of possible positions of the blood vessel cross-section and determine a second maximum value (e.g., referred to herein as a tracking of cylindrical cross-section maximum, or "TCC Maximum") that indicates a likelihood of the location of the blood vessel.

In any of the aspects or embodiments described above and herein, the plurality of ultrasonic transducers may include "N" number of ultrasonic transducers, where "N" is an integer, and only a subset of "M" number of said ultrasonic transducers, where "M" is an integer and a subset of M<N, may be actuated to produce incident ultrasonic signals on a time delay basis from a preceding ultrasonic transducer, the time delay corresponding to an amount of time it takes the incident ultrasonic signal to travel from the sensor to the blood vessel and a reflected ultrasonic signal to travel back to the sensor, wherein each of the M number of said ultrasonic sensors provides a better signal-to-noise (SNR) than those ultrasonic sensors in the plurality of ultrasonic sensors not in the subset.

According to an aspect of the present disclosure, a method of tracking a cross-section geometry of a blood vessel is provided. The method includes: a) non-invasively sensing a blood vessel using at least one sensor having a plurality of ultrasonic transducers on a periodic basis, the sensing producing signals representative of a plurality of features of the blood vessel; b) tracking the plurality of features of the blood vessel, using the signals representative of the plurality of features; and c) determining a cross-section geometry of the blood vessel as a function of time.

In any of the aspects or embodiments described above and herein, the produced signals may represent an ultrasonic image of the blood vessel.

In any of the aspects or embodiments described above and herein, the tracking step may include assigning a plurality of tracking windows to at least one of the plurality of features for each of a plurality of periodic frames, and the tracking step includes tracking a respective one of the plurality of features within a first tracking window from a first frame to a corresponding second tracking window from a second frame, the second frame subsequent to the first frame, and determining a first blood vessel diameter within the first frame and a second first blood vessel diameter within the second first frame.

In any of the aspects or embodiments described above and herein, the plurality of ultrasonic transducers may include "N" number of ultrasonic transducers, where "N" is an integer, and each ultrasonic transducer is actuated to produce incident ultrasonic signals on a time delay basis from a preceding ultrasonic transducer, the time delay corresponds to an amount of time it takes the incident ultrasonic signal to travel from the sensor to the blood vessel and a reflected ultrasonic signal to travel back to the sensor.

In any of the aspects or embodiments described above and herein, wherein for each of a plurality of possible positions of the blood vessel cross-section, the time delayed reflected signals are added to produce a collective signal and a maximum portion of the collective signal corresponding to an anterior wall of the blood vessel and a maximum portion of the collective signal corresponding to a posterior wall are multiplied to produce a maximum value.

In any of the aspects or embodiments described above and herein, the method may further include comparing the maximum value determined for each of the plurality of possible positions of the blood vessel cross-section and determine a second maximum value (e.g., referred to herein as a tracking of cylindrical cross-section maximum, or "TCC Maximum") that indicates a likelihood of the location of the blood vessel.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

DETAILED DESCRIPTION

This present disclosure describes a system 20 and method for tracking a blood vessel cross-section geometry, including changes in the cross-section geometry (e.g., changes in diameter) as a function of time in an image set or a data set. Embodiments of the present disclosure are configured to provide real-time, continuous, uninterrupted tracking of changes of the cross-section geometry of arteries and veins using ultrasonic sensing. This information can then be utilized to infer and/or predict possible states of the human and/or animal body (e.g., hypertension, hemorrhage, etc.), as well as physiological variables, such as but not limited to stroke volume, stroke volume variation, cardiac output, etc.

Figure 1:
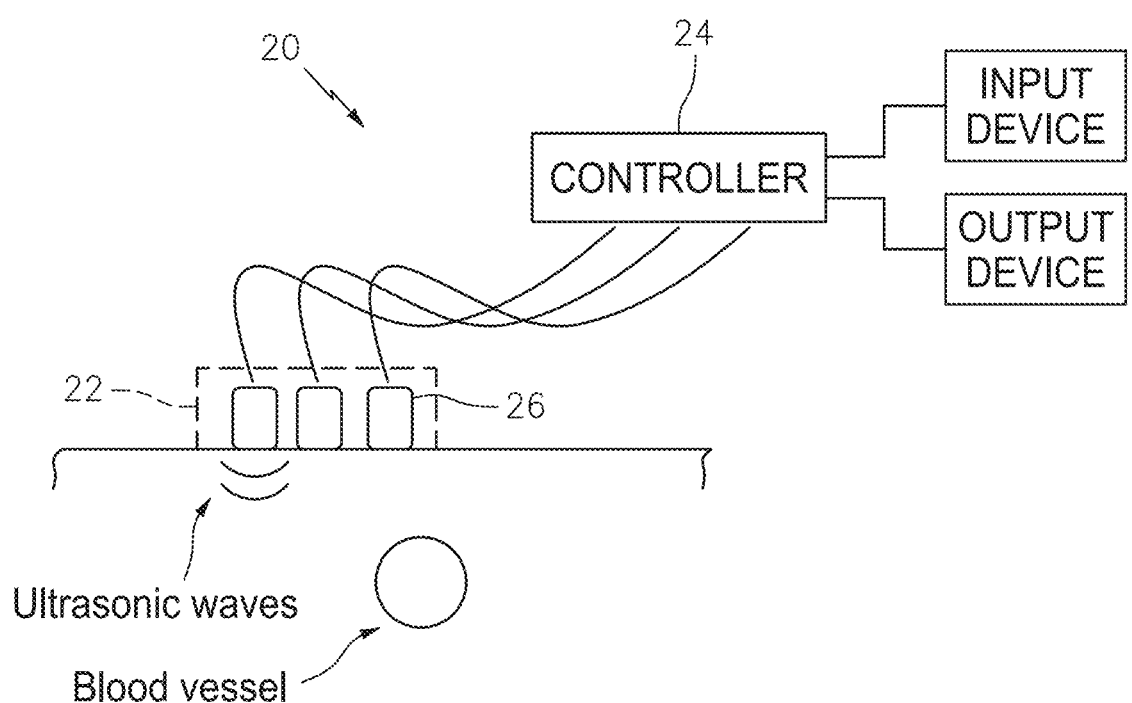
FIG. 1 is a diagrammatic illustration of a present disclosure system.

FIG. 1 shows an exemplary system 20 embodiment of the present disclosure that includes at least one sensor 22 and a controller 24. The sensor 22 includes at least one ultrasonic transducer 26. In many embodiments, the sensor 22 includes an array of ultrasonic transducers 26. The ultrasonic transducers 26 may be configured for two-way signal communication with the controller 24 via hard wire or by wireless means. Each ultrasonic transducer 26 is configured to both transmit and receive ultrasonic signals. In some embodiments, an ultrasonic transducer 26 may include one or more elements that both transmit and receive ultrasonic signals. In alternative embodiments, an ultrasonic transducer 26 may include one or more elements dedicated to transmitting ultrasonic signals and one or more elements dedicated to receiving ultrasonic signals. In those instances wherein an ultrasonic transducer includes a plurality of elements, the elements may be arranged in an array configuration. The term "ultrasonic signals" as used herein refers to the mechanical pressure waves produced and/or received by the transducer 26, which pressure waves are sometimes referred to as pressure waves, sound waves, sound pulses, acoustic waves, or the like. The transducers 26 are configurable to produce the ultrasonic signals at one or more predetermined frequencies and wavelengths; e.g., typically within the range of 1-10 MHz. Non-limiting examples of acceptable ultrasonic transducer 26 types include transducers having piezoelectric elements; e.g., PZT (lead zirconate titanate) based transducers, CMUT (capacitive micromachine) transducers, PMUT (piezoelectric micromachine) transducers, and like devices operable to transform mechanical energy into electrical energy and vice versa.

The controller 24 is in signal communication with the sensor(s) 22 to perform the functions described herein. The controller 24 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein to enable the system 20 to accomplish the same algorithmically and/or coordination of system 20 components. The controller 24 may include a single memory device or a plurality of memory devices. The present disclosure is not limited to any particular type of non-transitory memory device, and may include read-only memory, random access memory, volatile memory, non-volatile memory, static memory, dynamic memory, flash memory, cache memory, and/or any device that stores digital information. The controller 24 may include, or may be in communication with, an input device that enables a user to enter data and/or instructions, and may include, or be in communication with, an output device configured, for example to display information (e.g., a visual display or a printer), or to transfer data, etc. Communications between the controller 24 and other system 20 components may be via a hardwire connection or via a wireless connection.

The present disclosure can be used with a variety of different methodologies/apparatuses for detecting blood vessels, and features thereof, and is not therefore limited to use with any such methodology/apparatus. An example of such a methodology/apparatus is described in U.S. Provisional Patent Application No. 63/054,558, filed Jul. 21, 2020, entitled "System and Method for Non-Invasively Sensing a Blood Vessel", assigned to the present applicant. This exemplary system utilizes an array of ultrasound transducers disposed within a sensor and a controller in communication with the transducers in the array. The array of ultrasound transducers is configured to have at least a first ultrasonic transducer and a second ultrasonic transducer arranged in a column, with each transducer disposed in a row. The sensor is disposed on a skin surface of a subject so that the array column is substantially aligned along an axial length of a blood vessel. The first and second ultrasonic transducers are operated to interrogate the blood vessel disposed within the subject's tissue at the different axial positions, and to identify blood vessel wall features such as the anterior and posterior walls of the blood vessel.

Another example of such a methodology/apparatus is described in U.S. Provisional Patent Application No. 63/046,825 filed Jul. 1, 2020, entitled "Continuous Non-Invasive Analyte Measurement System and Method", also assigned to the present applicant. This system utilizes an excitation light source, an interrogation light source, a Fabry-Perot sensor, a light beam steering device, a light detector, and a controller. The controller is operable to control the light beam steering device to steer both the excitation light beam and the interrogation light beam relative to the Fabry-Perot sensor, and to measure an amount of an analyte within a blood vessel. The aforesaid system can be used to create a vasculature map of a tissue region being sensed, including identifying the location of blood vessels within the sensed tissue and the type of blood vessel (i.e., an artery or a vein) identified.

The methodologies/apparatuses for detecting blood vessels, including those identified above may be used with aspects of the present disclosure that track blood vessel cross-section geometry in an image domain. The same methodologies/apparatuses may be used with aspects of the present disclosure that track blood vessel cross-section geometry in a radio frequency domain.

During operation of at least some present disclosure systems 20, at least one sensor 22 is attached to the subject and positioned in detect a blood vessel of the subject. For those aspects of the present disclosure that track blood vessel cross-section geometry in an image domain, algorithmic instructions stored within the controller 24 (e.g., within a memory device portion of the controller 24, or independent of the controller 24) include a tracking function that utilizes a plurality of windows that enclose at least one local feature of a blood vessel. The at least one local feature is tracked between subsequent frames. The term "frame" as used herein refers to a collection of data (e.g., ultrasonic signals) that is periodically collected and analyzed. The frames may be described in terms of a first frame "N", a subsequent frame "N+1", a subsequent frame "N+2", etc. Each frame is based on periodically collected data, and the tracking function permits the one or more local features to be tracked as a function of time. The present disclosure is not limited to any particular data sampling periodic frequency and/or analysis periodic frequency, and can be configured with appropriate parameters for the task at hand. In some embodiments, the tracking periodic frequency may be such that the tracking is essentially continuous.

As will be described herein, some embodiments of the tracking function may be subject to convex constraints. The term "convex constraint" as used herein refers to an algorithmic constraint that corresponds to a convex function. Convex constraints are useful to improve the stability of the solution, decrease sub-optimal sequential operations, or improve the processing speed, or combinations thereof.

Some embodiments of the present disclosure are configured to track the mean diameter of an artery from beamformed ultrasound images. The term "mean" as used herein to modify the term diameter (i.e., "mean diameter") contemplates that a number is produced that is representative of a plurality of diameter values. The term "mean" is not limited to an arithmetic mean (i.e., the sum of the numbers divided by how many numbers are being averaged), and alternatively may be another measure of central tendency.

The present disclosure is well suited to track the mean diameter of a carotid artery, but is not limited thereto; e.g., as will be evident from the description herein, the present disclosure can be used to track a variety of different blood vessels, including tracking a cross-section area of the jugular and inferior vena cava veins, the descending aorta artery, arteries and veins of the arms, fingers, etc.

Figure 2:
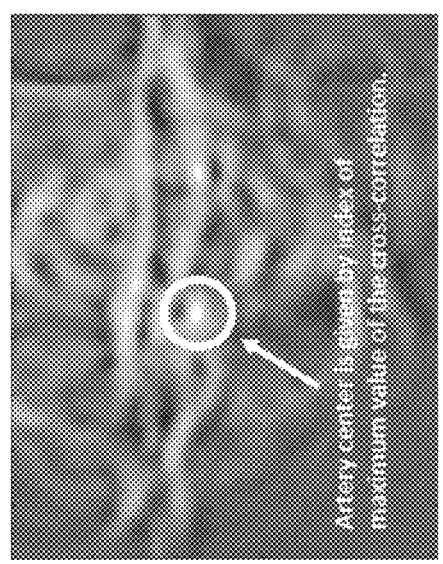
FIG. 2 is a diagrammatic illustration of an ultrasonic image cross-correlated with a kernel image as may be used in an initialization algorithm embodiment.
Figure 2:
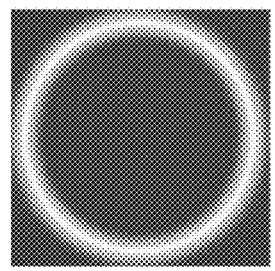
Figure 2:
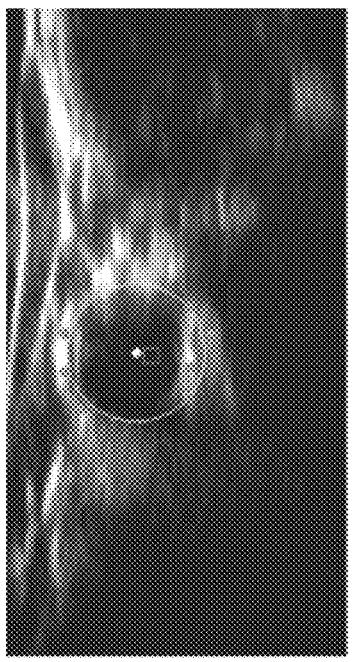

In some embodiments of the present disclosure, the controller 24 is configured (e.g., via stored instructions) to produce a set of tracking windows that may be automatically initialized within the cross-section of a blood vessel; e.g., using an initialization algorithm. The term "tracking window" as used herein, unless stated otherwise, generically refers to a search window or a reference window. A reference window defines the reference area or local feature in a frame N that is to be tracked in the search window in the subsequent frame N+1. Hence, search windows typically cover a larger area that the area covered by a reference window. Typically, the area of a reference window is centered in the area of the corresponding search window. An example of an initialization algorithm includes an index of the maximum value of the two-dimensional (2D) cross-correlation of an ultrasound image with a kernel image, where the kernel image resembles a smoothed version of the cross-section of interest as shown as an example in FIG. 2. In some embodiments, an initialization algorithm may utilize a convolutional neuronal network previously trained using a plurality of ultrasound images of vessel cross-sections labeled by trained subjects.

Figure 3:
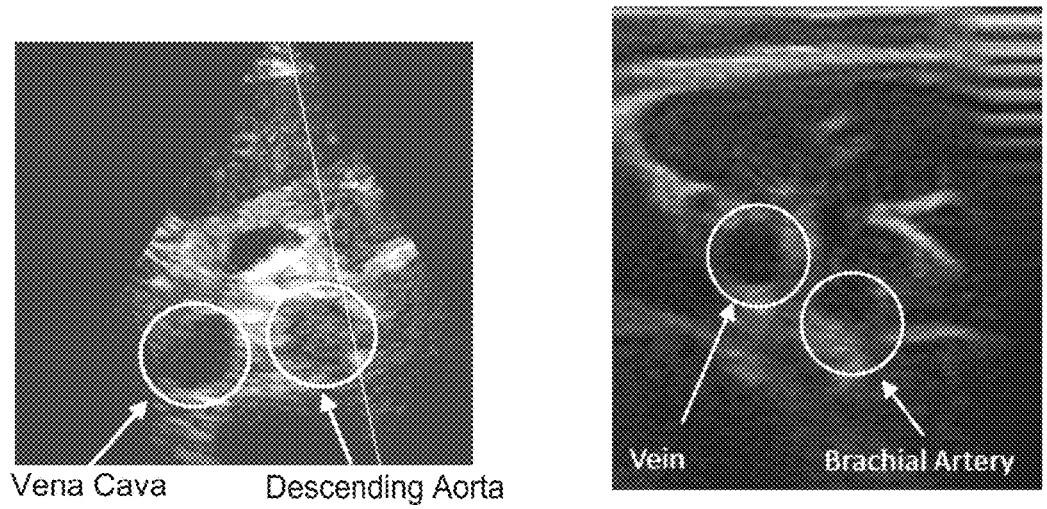
FIG. 3 illustrates examples of blood vessels that may be tracked in parallel using the present disclosure.
Figure 4:
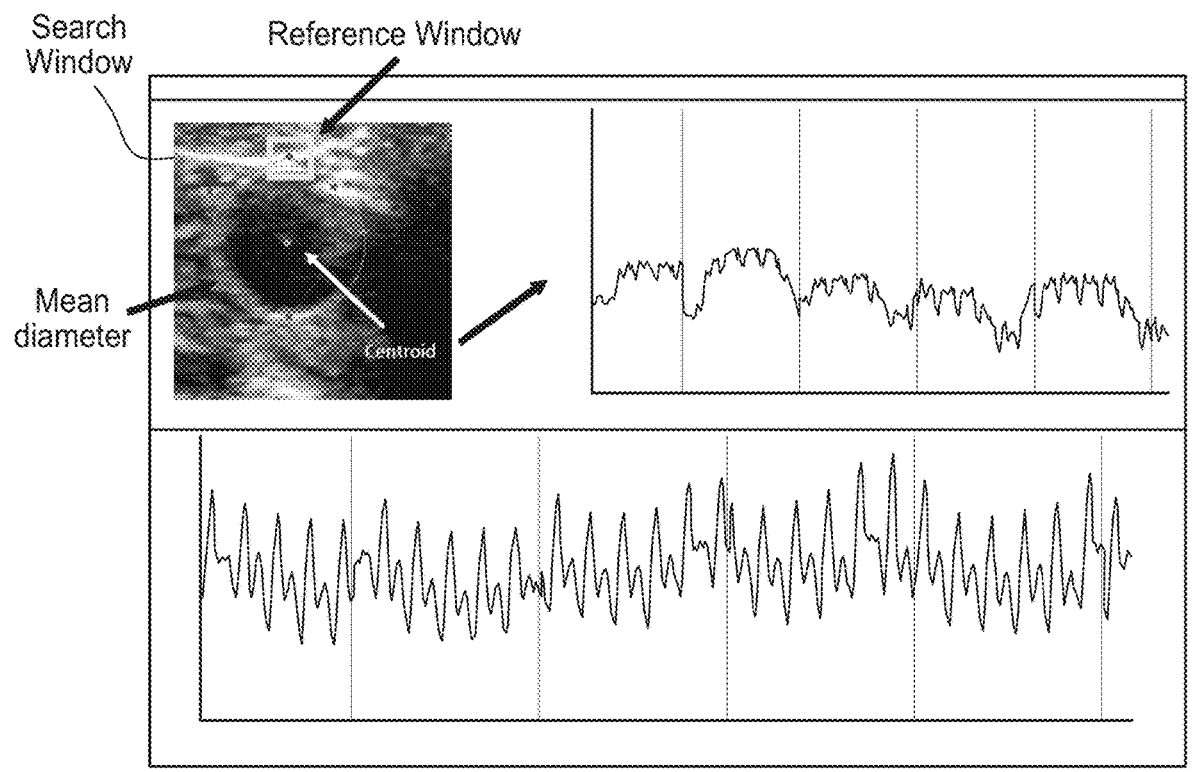
FIG. 4 illustrates an image of a blood vessel disposed within a tracking window, including a reference window, the centroid of the blood vessel, a graph of centroid values as a function of frames, the diameter of the blood vessel, and a graph of mean diameter values as a function of frames.

More than one vessel cross-section can be tracked at any time. For example, a jugular vein and a carotid artery, an inferior vena cava vein and a descending aorta artery, etc. FIG. 3 illustrates that in some embodiments cross-sections can be tracked in parallel.

After tracking windows have been established, a 2D cross-correlation is performed between each pair of search and reference windows (this may be performed after upsampling to increase the tracking resolution as described below). The aforesaid 2D cross-correlation may be performed in a frequency domain to achieve substantially better execution speeds. In some embodiments, the 2D cross-correlation may include a fast Fourier transform ("FFT") on the windows, multiplication of the transformed windows and a subsequent inverse FFT of the result (after zero padding to increase the tracking resolution in some instances). Subsequently, the algorithm searches for an extreme value of the cross-correlation. An extreme value may be determined, for example, utilizing the maximum of the absolute values. The index of the extreme value relative to a null or reference index indicates the new likely location or translation of the reference window (i.e., the local feature of interest) in the N+1 frame.

The present disclosure contemplates that 2D tapering of one or more of the windows, for example by using a 2D Hanning window before the 2D cross-correlation operation, may be beneficial in providing smoother cross-correlation results and/or to avoid errors that may be introduced by large function values close to the edge of windows.

In some embodiments, upsampling may be used to increase the granularity of the windows and hence the tracking resolution. The upsampling may be performed in the Fourier domain by zero-padding to achieve substantially faster execution speeds. Upsampling may include adding zeroed samples in between existing samples. For example, upsampling by a factor of two (2) will introduce one zeroed sample in between existing adjacent samples. Upsampling by a factor of three (3) will introduce two zeroed samples, etc. In some instances, highpass filtering may be used after upsampling to remove any unwanted frequency components added during the upsampling process. Upsampling by a factor to about five to about twenty (~5-~20) is believed to be useful, but the present disclosure is not limited to upsampling in this range. There is no theoretical limit as to how much a window can be upsampled other than computational or feature-to-noise ratio limits. The lack of a theoretical limit does not violate the Nyquist-Shannon law or equivalent diffraction-limited-resolution laws because the objective is not to resolve two features but to increase the accuracy with which the translation of the local features are tracked.

Each pair of tracking windows can be processed in parallel to substantially increase the execution speed.

In some instances, substantially extreme values in the search and/or reference windows can skew the result of the 2D cross-correlation. In other words, the most extreme value of the cross-correlation may not correspond with the actual translation of the feature that is being tracked. To compensate for this potential bias, some embodiments of the present disclosure utilize parallelizable, highly convex constraints, which are most suitable for parallel programming, preferably GPU programming. These constraints work by adding prior information about the global feature or features that are being tracked and by combining the information of the location of all or a substantial portion of the local features.

Figure 5:
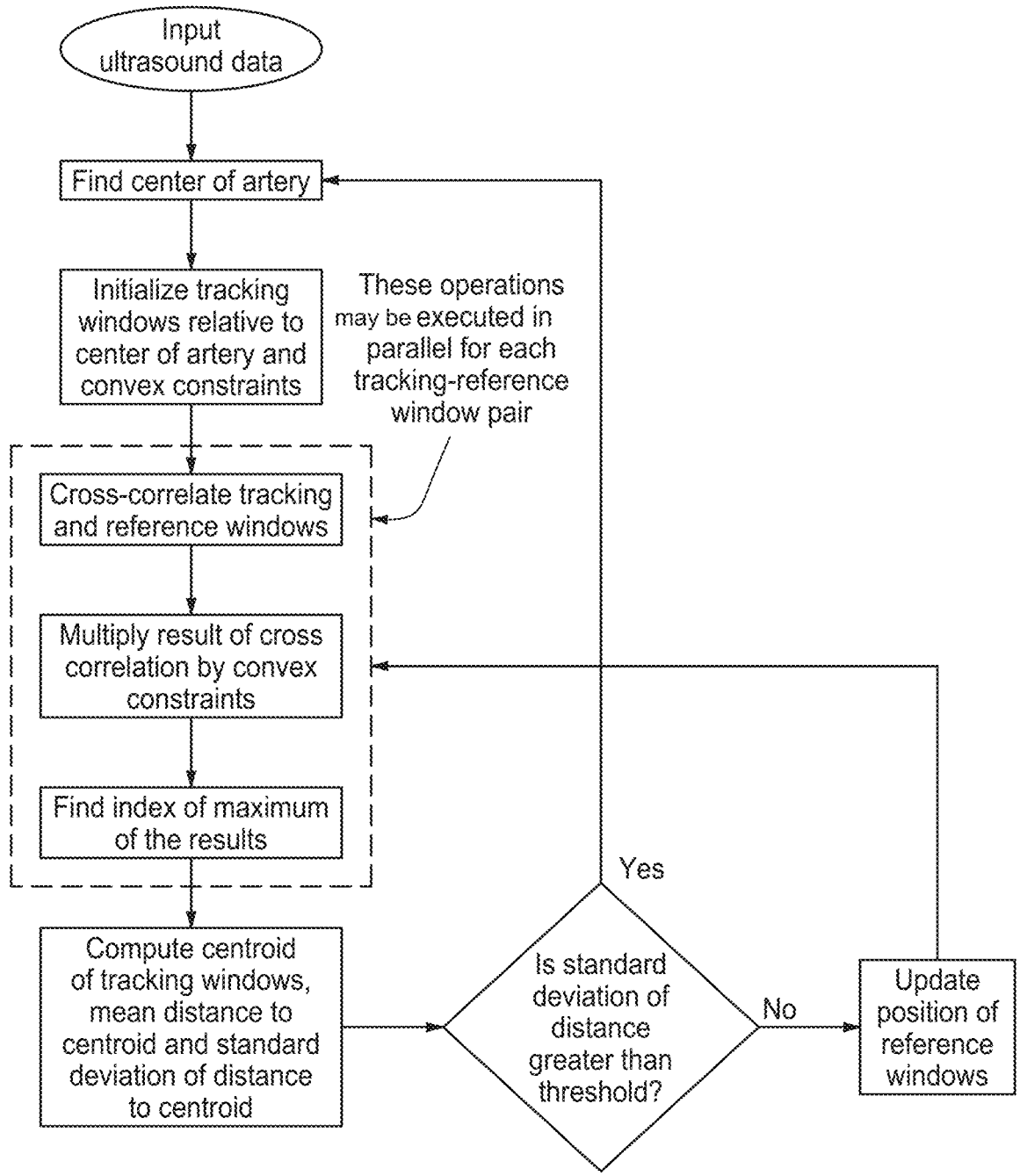
FIG. 5 is a flowchart illustrating an example of a tracking algorithm according to the present disclosure.

The present disclosure also recognizes that the tracking function may stray from the expected or correct values due to noisy data. In view thereof, some embodiments of the present disclosure may include a stability or confidence metric that, for example, can selectively trigger a reset of the tracking function. Some stability or confidence metrics may utilize the standard deviation of the mean distance from the center of a plurality of the tracking windows to their centroid or a variation of the standard deviation. A non-limiting example of a threshold stability trigger is a fraction of the mean distance from the center of a plurality of the tracking windows to their centroid. The flowchart of FIG. 5 provides an example of a tracking algorithm according to the present disclosure.

Figure 6:
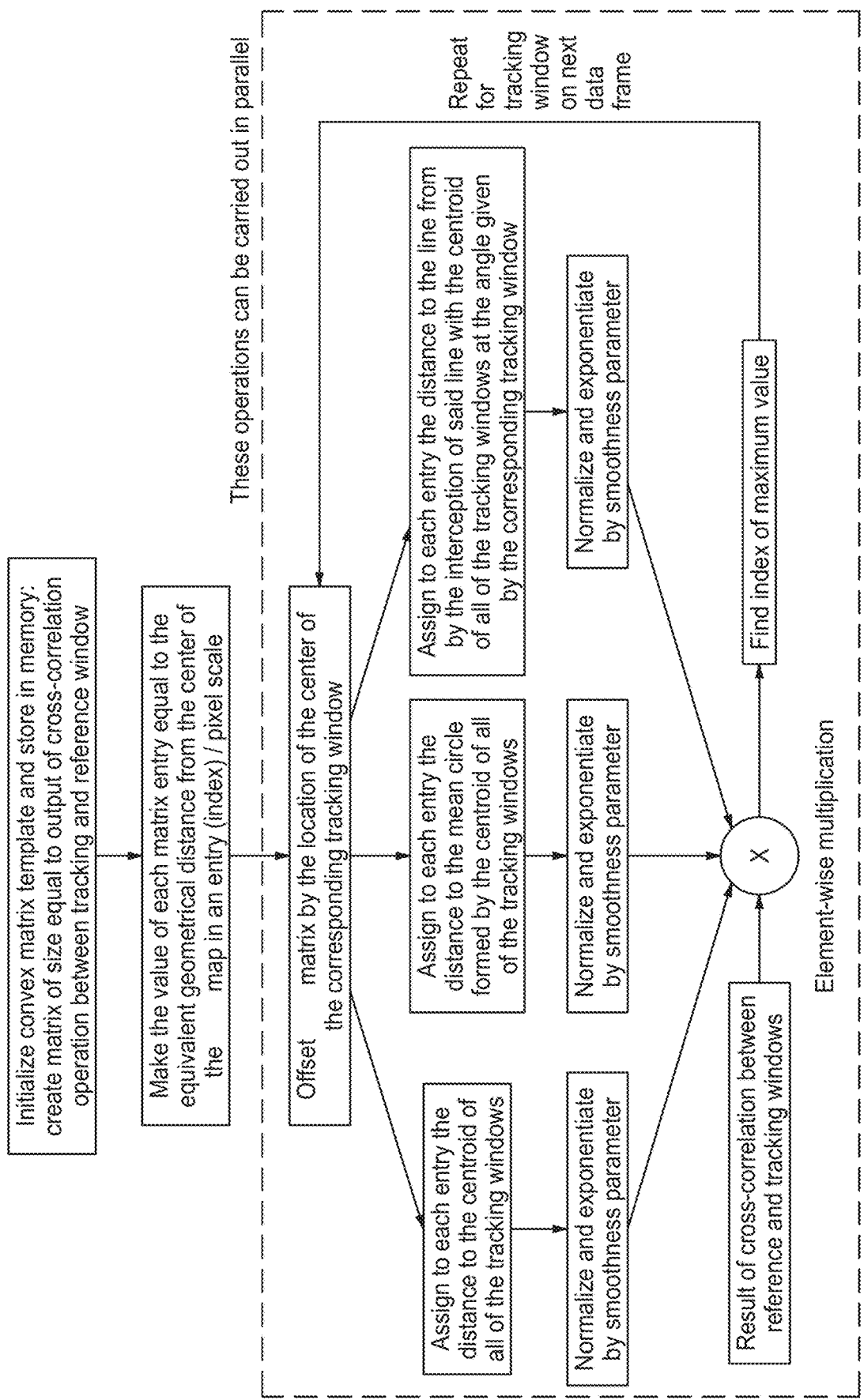
FIG. 6 is a flow chart illustrating an example of a procedure for computing a parallelizable, convex constraint.

The present disclosure may utilize a variety of different procedures for computing parallelizable, convex constraints, and therefore is not limited to any particular procedure. The flow chart of FIG. 6 illustrates an example of a procedure for computing a parallelizable, convex constraint. A map of size equal to the 2D cross-correlation between the windows is created (and preferentially stored locally in a parallel processor). The value of each entry in the map is made equal to the equivalent geometrical distance from the center of the map in a given scale. The map may be offset by the location of the center of the corresponding tracking window. A series of parallel, element-wise operations are performed over each element of the map in the parallel processors, which gives a substantial improvement in execution speed. The operations are the actual constraints that are to be implemented.

More than one constraint can be implemented, which may result in a plurality of weighted maps. The maps may be weighted based on knowledge, empirical data, testing, or any combination thereof, indicating the "value" of the respective constraint to provide accurate tracking for the application at hand; e.g., a first constraint that more positively influences the accuracy of the tracking than a second constraint would be assigned a greater weight. In some embodiments, constraints may be combined element-wise by, for example, element-wise multiplication, which gives a substantial improvement in execution speed. The constraint weighted maps may be combined element-wise in a parallel processor.

The weighed maps may be combined with the 2D cross-correlation by, for example, parallel, element-wise multiplication. The present disclosure recognizes that the weighed maps can in one extreme: (a) be ineffective if they are substantially constant and in another extreme (b) introduce unwanted local extreme values that incorrectly bias the result of the cross-correlation. To counteract these unwanted effects, some embodiments of the present disclosure may utilize a smoothness parameter. The smoothness parameter can, for example, be the exponent, and the smoothness operation an exponentiation after previous normalization of the weighted maps. As a result of tuning the smoothness of the weighed maps, the constraints are very likely to produce a substantially convex result. Thus, a gradient descent algorithm can be used to look for the most extreme value. Depending on the size of the windows and the computing elements, the gradient descent algorithm can perform substantially faster than element-by-element extreme value search.

Normalization of the weighed maps can be achieved, for example, by the absolute value of the difference (1−(value of map entry)/mean distance of the tracking windows to the centroid of all of the tracking windows).

The generation of the constraint maps may be inefficient for sequential processors. The present disclosure, however, provides a process that lends itself to parallel processing, and the overall processing speed can be increased substantially by using adequate parallel processing (e.g., GPUs).

When a new frame is ready to be processed, a sub-region of the search window in the previous N+1 frame offset by the location of the extreme value of the cross-correlation is then set as the new reference window, and an area for the search window is defined in the new frame centered at the equivalent location of the new reference window. One preferred way of setting the search window is by inferring the most likely location of the feature in the N+1 frame based on the trajectory history of the feature. For example, if the feature is moving at constant velocity V and located at position X in frame N, and the time elapsed between frames is T, the new expected location of the features will be X+V*T. This is not limited to the case where the feature moves with constant and non-constant acceleration. This invention recognizes that one efficient way of implementing this prediction of future location of the feature is by using a Kalman filter.

As stated above, embodiments of the present disclosure may utilize parallelizable, convex constraints, and some of these constraints utilize pre-determined information about a global feature or features. An example of such prior information may, for example, be that the local features are known to be arranged approximately in a circle (e.g., the cross-section of an artery-a global feature). In such a case, a constraint may be a weighed map with the inverse of the distance (or equivalent) from the weighed map entries to the circumference defined by all of the tracked local features as the mean distance to the centroid of the said local features. Another example of such prior information may be that blood vessels (e.g., arteries) have minimum and maximum possible diameters. In this case, a constraint may be that the mean distance to the centroid of the local features cannot exceed a minimum or maximum distance to the centroid. Another constraint may be the distance from the center of a tracking window to a line that intersects the centroid of all of the tracking windows at a given angle, where each said window is associated with a given angle only. This constraint is substantially beneficial in concentrating the number of tracking windows on the posterior and anterior walls of the cross-section rather than the side walls, where ultrasound is less sensitive. Another constraint may be the distance from the center of a tracking window to the centroid of all of the tracking windows. The above constraints are provided here as examples for illustrative purposes, and the present disclosure is not limited thereto.

The present disclosure recognizes that different reference and search window pairs may converge to a very close location after several iterations. This behavior can negatively affect a more general characterization of the global feature and, for example, the accuracy with which the diameter of the artery is estimated. Thus, another constraint that may prevent this undesirable convergence may be a weighed map of the mean distance between the adjacent tracking windows.

As an alternative to tracking a blood vessel cross-section in an image domain as described above, a blood vessel cross-section may be tracked utilizing signals directly from the ultrasonic transducers 26; i.e., in a radio frequency (RF) domain. To be clear, the term "radio frequency domain" as used herein does not refer to a "frequency domain" as that term is used above, which is used in regard to the transformation of a signal from its original domain to a frequency domain.

An ultrasonic transducer 26 produces an ultrasonic signal (i.e., wave) from its active area, which ultrasonic signal travels a distance through the subject's tissue to the blood vessel of interest (when the sensor 22 is applied to the subject). Single element ultrasonic transducers 26 may have a cylindrically shaped active area. In those ultrasonic transducers that have an array of elements, the elements may have rectangular shaped active areas. The active area of an ultrasonic transducer/element may be described as having a "relevant dimension" for the purpose of beam steering and/or beamforming, which term refers to the dimension of the active area that lies on a geometric plane associated with the vessel cross-section being sensed; e.g., typically the width of the active area.

Figure 7A:
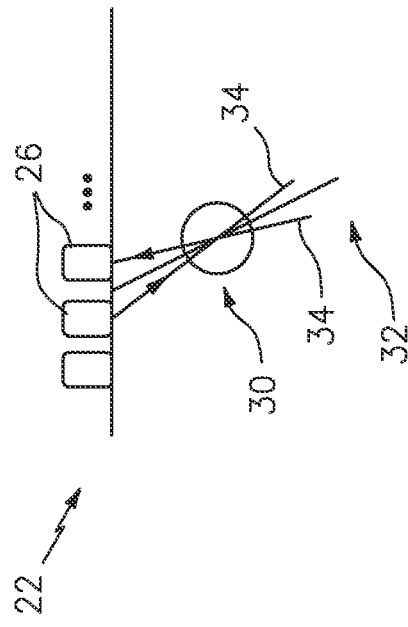
FIG. 7A is a diagrammatic illustration of ultrasonic waves emanating from an ultrasonic transducer within an array, indicating a path that ultrasonic signals will reflect from a substantially cylindrical cross-section of the blood vessel, and will be received by an ultrasonic transducer having an active area that both transmits and receives ultrasonic signals.
Figure 7B:
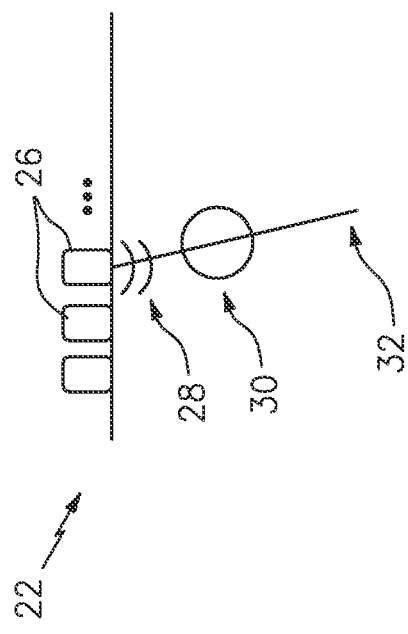
FIG. 7B is a diagrammatic illustration of ultrasonic waves emanating from an ultrasonic transducer within an array, indicating a path that ultrasonic signals will reflect from a substantially cylindrical cross-section of the blood vessel, and will be received when the ultrasonic signals are transmitted by a first ultrasonic transducer and received by a second ultrasonic transducer; e.g., a "pitch-catch" configuration.

In terms of a sensor 22 having ultrasonic transducers 26, if the relevant dimension of the active area of a transducer 26 is "small" relative to the propagation distance from the transducer 26 to the blood vessel (i.e., "small" meaning several times less), then due to the nature of wave propagation and reflection (i.e., Snell's law), ultrasonic waves 28 traveling the distance from the transducer 26 to the blood vessel 30 will reflect from the substantially cylindrical cross-section of the blood vessel 30 in a way that the most intensive reflected ultrasonic waves 28 correspond to the sections of the cylindrical cross-section border that are proximate an imaginary line 32 that intersects the center of the transducer 26 active area and the center of the cylindrical cross-section; e.g., See FIG. 7A. The imaginary line 32 corresponds to the line of strongest reflection from the cylindrical cross-section and that line 32 intersects the cylindrical cross-section. The embodiment shown in FIG. 7A may be referred to as a "pitch-echo" configuration wherein the same transducer transmits and receives. In terms of a sensor 22 having transmitting ultrasonic transducers 26 that are independent of receiving ultrasonic transducers 26 (e.g., a "pitch-catch" configuration wherein different transducers transmit and receive), and again assuming that the active area diameter of the transducers 26 are small, then the most intensive reflected ultrasonic waves correspond to the sections of the cylindrical cross-section border of the blood vessel 30 that lie close to an imaginary line 32 that bisects the imaginary lines 34 that intersect the center of the respective pitch-catch transducers 26 and the center of the cylindrical cross-section; e.g., See FIG. 7B. The imaginary line 32 corresponds to the line of strongest reflection from the cylindrical cross-section and that line 32 intersects the cylindrical cross-section and bisects the imaginary lines 34 from the pulse-echo transmit-receive paths. These propagation characteristics may be taken into account during analysis of the reflected ultrasonic signals.

Figure 8:
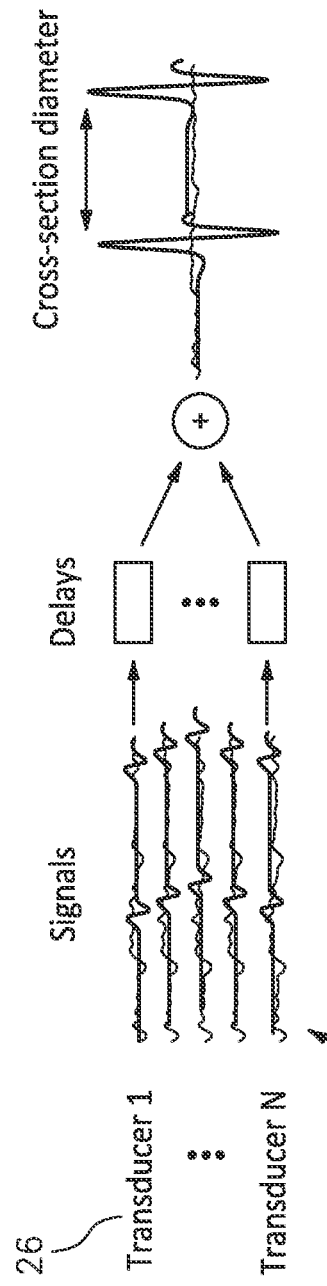
FIG. 8 is a diagrammatic illustration of an exemplary present disclosure system configuration wherein the ultrasonic transducers are operated in a time-delayed manner.

In those embodiments wherein the sensor 22 includes a plurality of ultrasonic transducers 26, the controller 24 may be algorithmically configured to operate the ultrasonic transducers 26 on a time delay basis. FIG. 8 diagrammatically illustrates an exemplary present disclosure system 20 configuration wherein the ultrasonic transducers 26 are operated in a time-delayed manner; e.g., "N" number of ultrasonic transducers (where "N" is an integer), and the actuation of each transducer 26 is time delayed from the preceding transducer 26. The magnitude of the time delay between ultrasonic transducers 26 may be chosen to correspond to the time it takes an ultrasonic signal to travel the distance from the ultrasonic transducer 26 to the center of the cylindrical cross-section of the vessel and back to the transducer 26. The time delayed operation of the respective ultrasonic transducers 26 produces receipt of time delayed reflected ultrasonic signals. The time delayed signals from the respective ultrasonic transducers 26 may be added. The resulting collective reflected signal maximizes the boundaries of a cylindrical cross-section of a blood vessel being interrogated relative to background noise and/or interference. More specifically, the collective reflected signal is expected to have greater amplitudes or maxima that correspond to the posterior and anterior boundaries of the cylindrical cross-section in comparison to the background noise and/or interference present in the signals, and thereby provide an improved signal-to-noise ratio (SNR).

Figure 9:
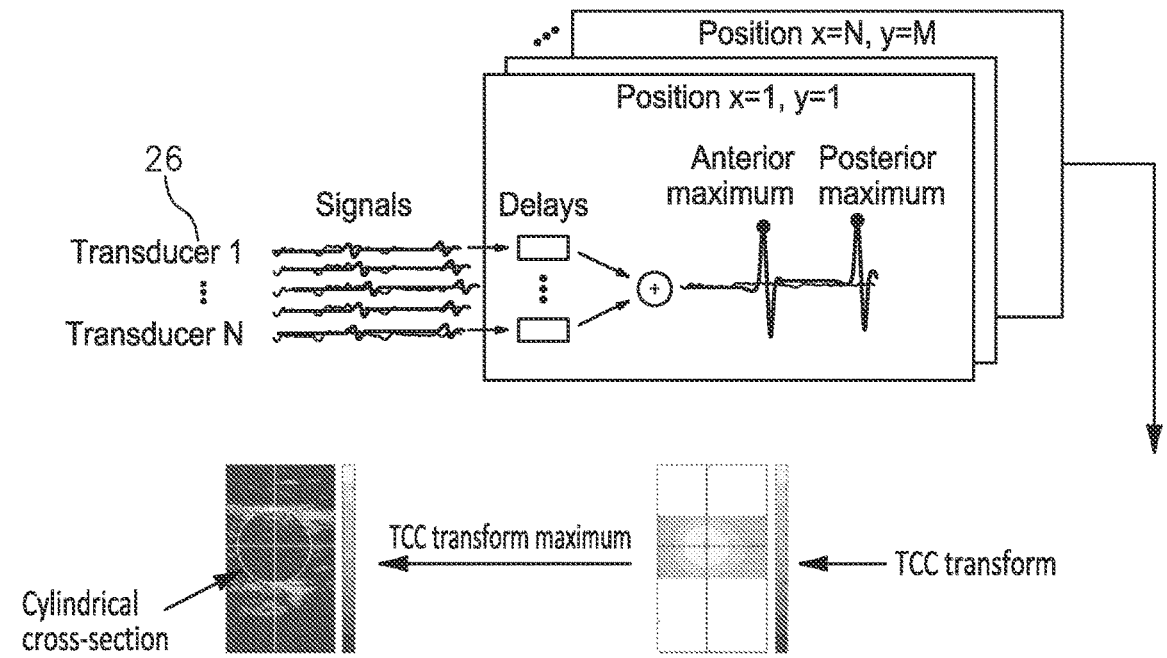
FIG. 9 is a diagrammatic illustration of a TCC transform.
Figure 10:
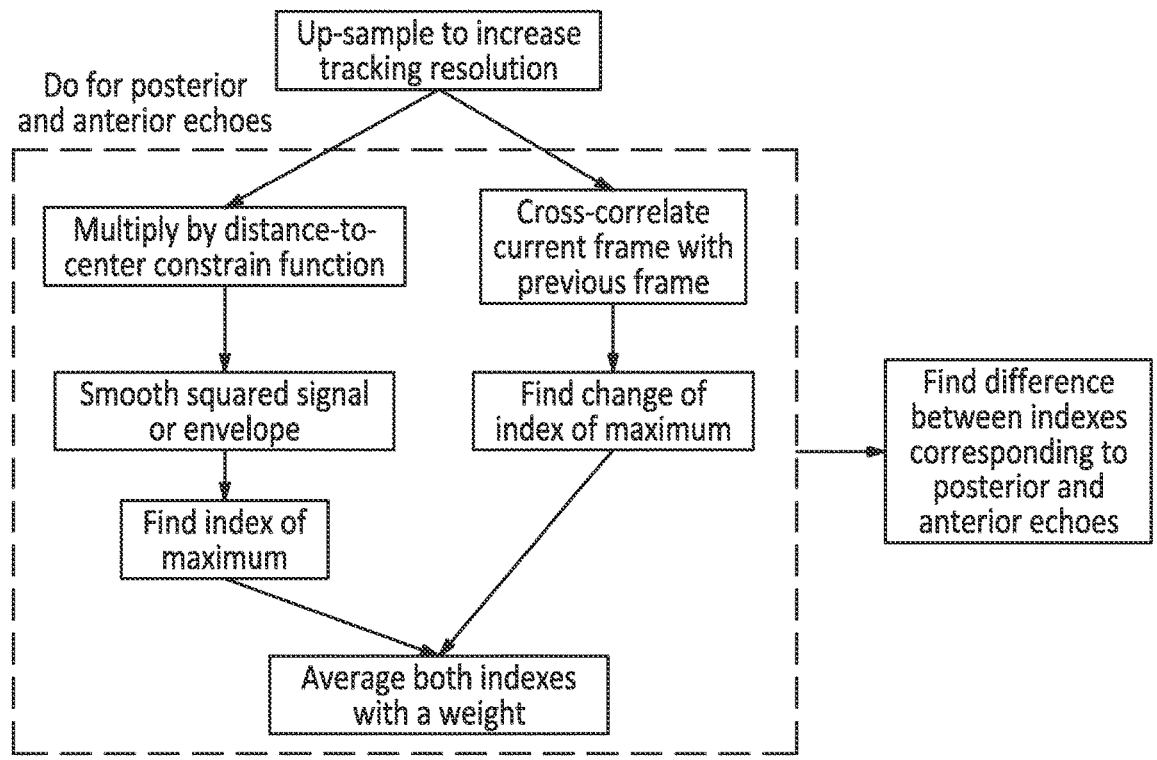
FIG. 10 is a flow chart illustrating an embodiment of a process for tracking changes of a cylindrical cross-section.

In some embodiments of the present disclosure, the controller 24 may be configured (e.g., via stored instructions) to utilize a cylindrical cross-section vessel tracking transform, referred to hereinafter as the "tracking of cylindrical cross-section transform" or "TCC transform". A TCC transform may be used to find the center of the cylindrical cross-section and cross-section profile with maximum peak signal to background ratio. A non-limiting example of a TCC transform is diagrammatically shown in FIG. 9. The flow chart shown in FIG. 10 illustrates an embodiment of a process for tracking changes of a cylindrical cross-section. Delayed ultrasonic signals are produced and added as described above from the array of transducers 26 (or subsets thereof), then the maximum of the portions of the signals understood to correspond to the posterior and anterior walls of the cylindrical cross-section are multiplied; e.g., for every X and Y position. This process may be repeated for a defined set of possible positions of the cylindrical cross-section. A maximum of this result (i.e., the maximum of the TCC transform, or "TCC Maximum"), corresponds to the most likely location of the center of the cylindrical cross-section and therefore the corresponding delays correspond to the profile of the cylindrical cross-section that has the highest peak-to-background-noise or -interference ratio. One application of the TCC transform provides a high speed technique for determining the center of a cylindrical cross-section vessel.

In some embodiments of the present disclosure, instead of determining the maximum of the portions of the signals that substantially correspond to the posterior and anterior walls of the cylindrical cross-section, and subsequently multiplying them as described above to determine the location of a cylindrical cross-section center, other metrics could also be used to determine the same. For example, the total energy of the portions of the signals that substantially correspond to the posterior and anterior walls of the cylindrical cross-section could be multiplied or added.

In some embodiments, the TCC transform may include pre-calculating a plurality of delay maps for a substantial number of possible locations of the cylindrical cross-section and storing them in the memory of the processing unit. The aforesaid delay maps may be used subsequently to expedite the TCC transform computation process.

In some embodiments, the controller 24 may be configured to compute a TCC transform using only select ultrasonic transducers 26 within the transducer array of a sensor 22; e.g., using only those ultrasonic transducers 26 that are situated to provide a favorable SNR, which may be less than all of the transducers 26 within the array. Using this technique, the TCC transform can be computed more efficiently and rapidly. Ultrasonic transducers 26 typically have a signal radiation pattern that radiates more energy normal to their active area rather than tangential to their active area, and therefore using signals from transducers 26 that have a poor radiation contribution relative to the vessel of interest decreases the SNR. By using only those ultrasonic transducers 26 that fall within a given horizontal distance (e.g., a lateral distance) between the respective ultrasonic transducer 26 and the location of the blood vessel of interest, the SNR improves and the computing speed of the process is improved (e.g., less signal processing). Alternatively, a TCC transform can be computed using only those ultrasonic transducers 26 positioned such that the blood vessel of interest falls within a given angle with respect to the plane of the effective aperture of the transducer 26. The present disclosure is not limited to these techniques and other criteria for selectively choosing the participating ultrasonic transducers 26 may be used alternatively.

In some embodiments of the present disclosure, an initial TCC transform may be computed over an entire area of interest. This may be referred to as a "coarse" TCC transform. Subsequently, one or more secondary TCC transforms may be computed over one or more subsets of the area of interest. Each of these may be referred to as a "finer" TCC transform. The coarse TCC transform may be used to determine the approximate location of the center of the artery, which corresponds to the maximum of the TCC transform, and subsequently run the finer TCC transform on only a subset of substantially adjacent or proximal entries or elements in the delay map that correspond to the coarse TCC transform to determine the position of the center of the artery more accurately.

Figure 11:
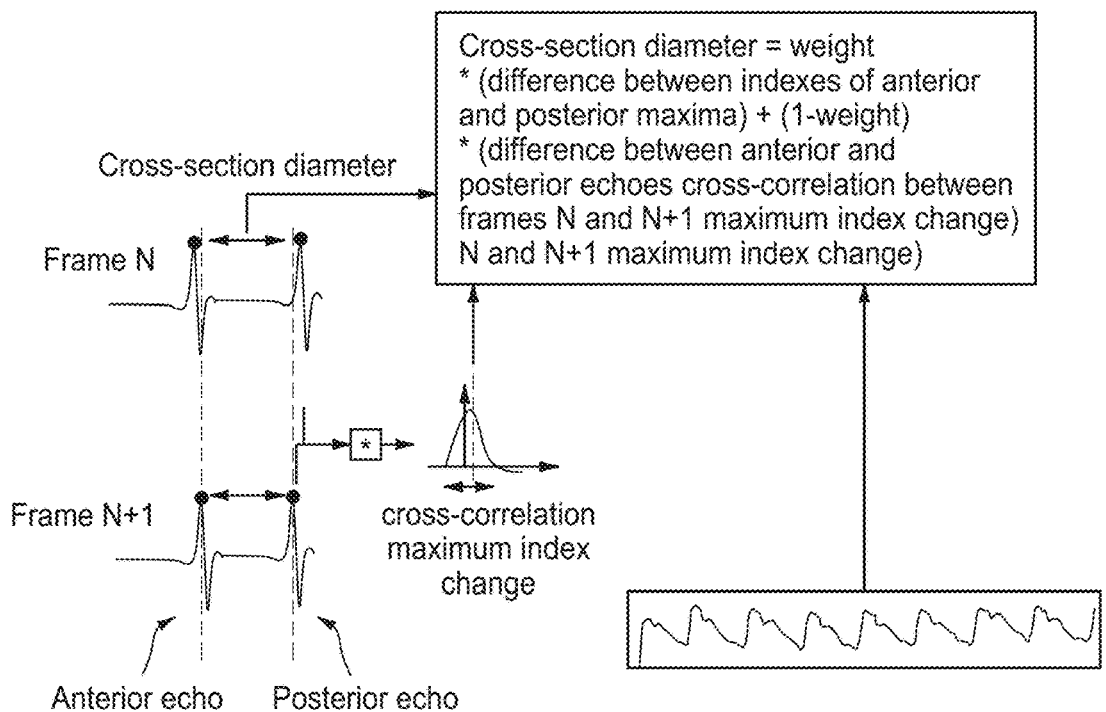
FIG. 11 is a diagrammatic illustration of an example of how the changes in the cylindrical cross-section profile may be calculated according to the present disclosure.
Figure 12:
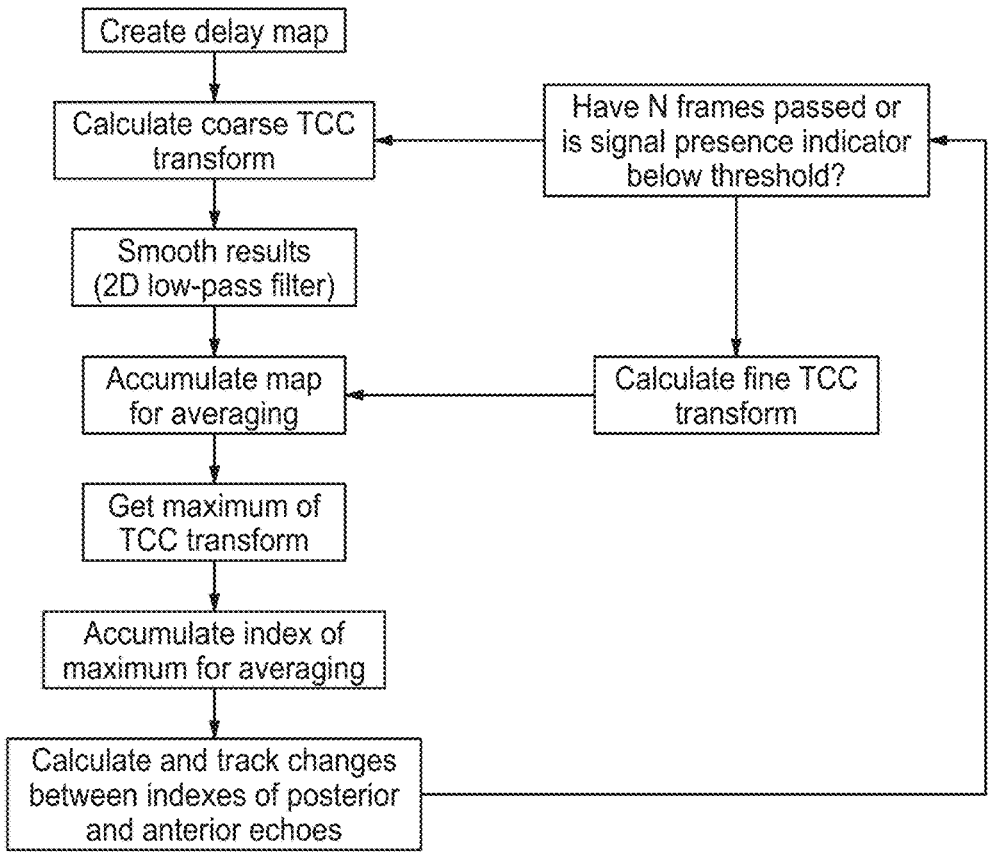
FIG. 12 is a flow chart illustrating an example of how changes in a cylindrical cross-section diameter may be determined using a TCC transform to track changes of cylindrical cross-section diameter.

The present disclosure recognizes that the time delays corresponding to the maximum of the TCC transform will likely yield a cross-section profile of the cylindrical cross-section that has the highest signal to background noise and/or interference ratio. The changes in the cylindrical cross-section that correspond to the cross-section diameter changes may be computed from this profile as follows. FIG. 11 diagrammatically illustrates an example of how the changes in the cylindrical cross-section profile may be calculated. The flow chart shown in FIG. 12 illustrates an example of how changes in a cylindrical cross-section diameter may be determined to track changes of cylindrical cross-section diameter.

The following operations may be executed (e.g., by the controller 24 via stored instructions) for each portion of the cross-section profile that corresponds to the anterior and posterior sections of the cylindrical cross-section. First, the signals may be upsampled to increase tracking resolution. Next, an index of absolute maximum may be computed, for example, using the following processes: a) the signals are multiplied by a vector whose values correlate negatively with the distance to the center of the vector to promote tracking maxima closer to the center of the profile; b) the signals are squared and smoothed or the envelope extracted; and c) the indexes of maxima corresponding to each anterior and posterior wall sections of the cylindrical cross-section may be computed. Next, an index of cross-correlation between current and previous (frames) signal maxima for each section of the signal that corresponds to the anterior and posterior wall of the cylindrical cross-section may be computed. Next, both the absolute and relative index change may be combined using a weighted average. The vessel cross-section diameter may be calculated as a weighted average of: a) the distance between the maxima of the first and second halves of the signal that results after adding the delayed signals and corresponding to the posterior and anterior walls of the cylindrical cross-section; and b) the relative change of the index of the cross-correlation maximum between the current and previous signal (frames) for each section of the signal that corresponds to the posterior and anterior wall of the cylindrical cross-section. The aforesaid processes are an example of how the changes in the vessel cylindrical cross-section may be determined in a radio frequency domain is provided for illustrative purposes, and the present disclosure is not limited thereto.

The above described techniques for tracking the cross-section geometry in an image domain or a radio frequency domain may be performed on a time-periodic basis that is useful for the application at hand, including being performed so as to provide tracking that is essentially continuous. The present disclosure is not limited to the aforesaid tracking techniques being performed on any particular frequency.

While various inventive aspects, concepts and features of the disclosures may be described and illustrated herein as embodied in combination in the exemplary embodiments, these various aspects, concepts, and features may be used in many alternative embodiments, either individually or in various combinations and sub-combinations thereof. Unless expressly excluded herein all such combinations and sub-combinations are intended to be within the scope of the present application. Still further, while various alternative embodiments as to the various aspects, concepts, and features of the disclosures—such as alternative materials, structures, configurations, methods, devices, and components, alternatives as to form, fit, and function, and so on—may be described herein, such descriptions are not intended to be a complete or exhaustive list of available alternative embodiments, whether presently known or later developed. Those skilled in the art may readily adopt one or more of the inventive aspects, concepts, or features into additional embodiments and uses within the scope of the present application even if such embodiments are not expressly disclosed herein.

Additionally, even though some features, concepts, or aspects of the disclosures may be described herein as being a preferred arrangement or method, such description is not intended to suggest that such feature is required or necessary unless expressly so stated. Still further, exemplary or representative values and ranges may be included to assist in understanding the present application, however, such values and ranges are not to be construed in a limiting sense and are intended to be critical values or ranges only if so expressly stated.

Moreover, while various aspects, features and concepts may be expressly identified herein as being inventive or forming part of a disclosure, such identification is not intended to be exclusive, but rather there may be inventive aspects, concepts, and features that are fully described herein without being expressly identified as such or as part of a specific disclosure, the disclosures instead being set forth in the appended claims. Descriptions of exemplary methods or processes are not limited to inclusion of all steps as being required in all cases, nor is the order that the steps are presented to be construed as required or necessary unless expressly so stated. The words used in the claims have their full ordinary meanings and are not limited in any way by the description of the embodiments in the specification.

What is claimed is:

1. A system for tracking a cross-section geometry of a blood vessel, comprising:
   at least one sensor having a plurality of ultrasonic transducers configured to non-invasively sense a blood vessel and provide signals representative of the blood vessel; and
   a controller in communication with the at least one sensor and a non-transitory memory storing instructions, which instructions when executed cause the controller to:
   control the plurality of ultrasonic transducers to periodically sense the blood vessel and produce signals representative of an ultrasonic image of a plurality of features of the blood vessel; and
   track the plurality of features of the blood vessel, using the signals representative of the plurality of features to determine a cross-section geometry of the blood vessel as a function of time;
   wherein the tracking includes assigning a first plurality of windows to a first feature of the plurality of features within a first frame, and a second plurality of windows to the first feature within a second frame, wherein the second frame is subsequent to the first frame, and performing a two dimensional cross-correlation between the signals representative of the first feature within the first frame and the signals representative of the first feature within the second frame using at least one convex constraint.

2. The system of claim 1, wherein the instructions when executed cause the controller to track the plurality of features in parallel.

3. The system of claim 1, wherein the instructions when executed cause the controller to assign a third plurality of windows to a second feature of the plurality of features within the first frame, and a fourth plurality of windows to the second feature within the second frame, and to perform a two dimensional cross-correlation between the signals representative of the second feature within the first frame and the signals representative of the second feature within the second frame using at least one convex constraint, and wherein the first and second plurality of windows are tracked in parallel with the third and fourth plurality of windows.

4. The system of claim 3, wherein the two dimensional cross-correlation between the signals representative of the first feature within the first frame and the signals representative of the first feature within the second frame is performed using a plurality of substantially convex constraints, each assigned a relative weight, and wherein the two dimensional cross-correlation between the signals representative of the second feature within the first frame and the signals representative of the second feature within the second frame is performed using a plurality of substantially convex constraints, each assigned a relative weight.

5. A system for tracking a cross-section geometry of a blood vessel, comprising:
- at least one sensor having a plurality of ultrasonic transducers configured to non-invasively sense a blood vessel and provide signals representative of the blood vessel; and
- a controller in communication with the at least one sensor and a non-transitory memory storing instructions, which instructions when executed cause the controller to:
  - control the plurality of ultrasonic transducers to periodically sense the blood vessel and produce signals representative of a plurality of features of the blood vessel; and
  - wherein the periodic sensing includes controlling each ultrasonic transducer to produce incident ultrasonic signals on a time delay basis from a preceding ultrasonic transducer producing incident ultrasonic signals, wherein the time delay corresponds to an amount of time it takes the incident ultrasonic signals to travel from the ultrasonic transducer to the blood vessel and a reflected ultrasonic signal to travel back to the ultrasonic transducer; and
  - track the plurality of features of the blood vessel, using the signals representative of the plurality of features to determine a cross-section geometry of the blood vessel as a function of time.

6. The system of claim 5, wherein the time delayed reflected signals are added to produce a collective signal, and wherein a maximum portion of the collective signal corresponding to an anterior wall of the blood vessel and a maximum portion of the collective signal corresponding to a posterior wall are multiplied.

7. The system of claim 5, wherein for each of a plurality of possible positions of the blood vessel cross-section, the time delayed reflected signals are added to produce a collective signal, and wherein a maximum portion of the collective signal corresponding to an anterior wall of the blood vessel and a maximum portion of the collective signal corresponding to a posterior wall are multiplied to produce a maximum value.

8. The system of claim 7, wherein the instructions when executed cause the controller to compare the maximum value determined for each of the plurality of possible positions of the blood vessel cross-section and to determine a second maximum value.

9. A system for tracking a cross-section geometry of a blood vessel, comprising:
- at least one sensor having a plurality of ultrasonic transducers configured to non-invasively sense a blood vessel and provide signals representative of the blood vessel; and
- a controller in communication with the at least one sensor and a non-transitory memory storing instructions, which instructions when executed cause the controller to:
  - control the plurality of ultrasonic transducers to periodically sense the blood vessel and produce signals representative of a plurality of features of the blood vessel; and
  - track the plurality of features of the blood vessel, using the signals representative of the plurality of features to determine a cross-section geometry of the blood vessel as a function of time;
- wherein the plurality of ultrasonic transducers includes "N" number of ultrasonic transducers, where "N" is an integer, and only a subset of "M" number of said ultrasonic transducers, where "M" is an integer and M<N, are actuated to produce incident ultrasonic signals on a time delay basis from a preceding ultrasonic transducer, the time delay corresponding to an amount of time it takes the incident ultrasonic signal to travel from the sensor to the blood vessel and a reflected ultrasonic signal to travel back to the sensor, wherein each of the M number of said ultrasonic transducers provides a better signal-to-noise ratio (SNR) than those ultrasonic transducers in the plurality of ultrasonic transducers not in the subset.

10. A method of tracking a cross-section geometry of a blood vessel, comprising:
- non-invasively sensing a blood vessel using at least one sensor having a plurality of ultrasonic transducers on a periodic basis, the sensing producing signals representative of an ultrasonic image of a plurality of features of the blood vessel;
- tracking the plurality of features of the blood vessel, using the signals representative of the plurality of features, the tracking including assigning a plurality of tracking windows to at least one of the plurality of features for each of a plurality of periodic frames, and tracking a respective one of the plurality of features within a first tracking window from a first frame to a corresponding second tracking window from a second frame, the second frame subsequent to the first frame, and determining a first diameter value of the blood vessel within the first frame and a second diameter value of the blood vessel within the second frame; and
- determining a cross-section geometry of the blood vessel as a function of time using the first diameter value of the blood vessel and the second diameter value of the blood vessel.

11. The method of claim 10, wherein the plurality of ultrasonic transducers includes "N" number of ultrasonic transducers, where "N" is an integer, and each ultrasonic transducer is actuated to produce incident ultrasonic signals on a time delay basis from a preceding ultrasonic transducer, wherein the time delay corresponds to an amount of time it takes the incident ultrasonic signal to travel from the sensor to the blood vessel and a reflected ultrasonic signal to travel back to the sensor.

12. The method of claim 10, wherein for each of a plurality of possible positions of the blood vessel cross-section, the time delayed reflected signals are added to produce a collective signal, and wherein a maximum portion of the collective signal corresponding to an anterior wall of the blood vessel and a maximum portion of the collective signal corresponding to a posterior wall are multiplied to produce a maximum value.

13. The method of claim 12, further comprising comparing the maximum value determined for each of the plurality of possible positions of the blood vessel cross-section and determining a second maximum value.

* * * * *